United States Patent
Majeti et al.

(10) Patent No.: US 7,166,235 B2
(45) Date of Patent: Jan. 23, 2007

(54) COMPOSITIONS COMPRISING ANIONIC FUNCTIONALIZED POLYORGANOSILOXANES FOR HYDROPHOBICALLY MODIFYING SURFACES AND ENHANCING DELIVERY OF ACTIVE AGENTS TO SURFACES TREATED THEREWITH

(75) Inventors: Satyanarayana Majeti, Middletown, OH (US); Elizabeth Ann Brown Reno, Fairfield, OH (US); Stephen Andras Kovacs, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 262 days.

(21) Appl. No.: 10/430,520

(22) Filed: May 6, 2003

(65) Prior Publication Data

US 2003/0211050 A1 Nov. 13, 2003

Related U.S. Application Data

(60) Provisional application No. 60/378,997, filed on May 9, 2002.

(51) Int. Cl.
C14C 9/00 (2006.01)
A61Q 11/00 (2006.01)

(52) U.S. Cl. ............... 252/8.57; 252/8.63; 424/49; 424/52; 424/53; 424/55; 428/429; 428/450; 528/25; 528/26; 528/31

(58) Field of Classification Search ............... 528/25, 528/26, 31
See application file for complete search history.

(56) References Cited

U.S. PATENT DOCUMENTS

| | | |
|---|---|---|
| 3,560,544 A | 2/1971 | Haluska |
| 4,342,742 A | 8/1982 | Sebag et al. |
| 4,501,619 A | 2/1985 | Gee |
| 4,563,347 A | 1/1986 | Starch |
| 4,587,320 A | 5/1986 | Swihart |
| 4,658,049 A | 4/1987 | Nakano et al. |
| 4,701,269 A | 10/1987 | Bay et al. |
| 4,844,888 A | 7/1989 | Zawadzki |
| 4,857,212 A | 8/1989 | Ona et al. |
| 4,876,152 A | 10/1989 | Kang |
| 4,931,062 A | 6/1990 | Bay et al. |
| 4,944,978 A | 7/1990 | Pipkins |
| 5,015,700 A | 5/1991 | Herzig et al. |
| 5,032,387 A | 7/1991 | Hill et al. |
| 5,057,308 A | 10/1991 | Hill et al. |
| 5,063,044 A | 11/1991 | Kohl et al. |
| 5,078,988 A | 1/1992 | Lin et al. |
| 5,154,915 A | 10/1992 | Weber et al. |
| 5,165,913 A | 11/1992 | Hill et al. |
| 5,188,822 A | 2/1993 | Viccaro et al. |
| 5,210,251 A | 5/1993 | Ohashi et al. |
| 5,248,783 A | 9/1993 | O'Lenick |
| 5,280,019 A | 1/1994 | Klimisch |
| 5,296,625 A | 3/1994 | O'Lenick, Jr. et al. |
| 5,422,098 A | 6/1995 | Rolla et al. |
| 5,427,770 A | 6/1995 | Viccaro et al. |
| 5,447,997 A | 9/1995 | Raleigh et al. |
| 5,504,233 A | 4/1996 | Bindl et al. |
| 5,536,304 A | 7/1996 | Coppens et al. |
| 5,702,490 A | 12/1997 | Kneip et al. |
| 5,759,523 A | 6/1998 | Hughes et al. |
| 5,827,505 A | 10/1998 | Hughes et al. |
| 5,856,282 A | 1/1999 | Hughes |
| 5,888,491 A | 3/1999 | Mitra et al. |
| 5,900,231 A * | 5/1999 | Richard et al. ............... 424/60 |
| 6,004,538 A | 12/1999 | Hughes et al. |
| 6,007,801 A | 12/1999 | Hossel et al. |
| 6,024,891 A | 2/2000 | Hughes |
| 6,129,906 A | 10/2000 | Steventon |

(Continued)

FOREIGN PATENT DOCUMENTS

JP 04/120014 4/1992

OTHER PUBLICATIONS

Definition of "detergent" from Merriam-Webster Online Dictionary.*

(Continued)

Primary Examiner—Marc S. Zimmer
(74) Attorney, Agent, or Firm—Emelyn L. Hiland

(57) ABSTRACT

Disclosed are compositions and methods for treating and modifying surfaces and for enhancing delivery of active agents to surfaces treated therewith, wherein the compositions comprise siloxane polymers functionalized with pendant moieties comprising two or more anionic groups, at least one anionic group being a carboxy group. When applied to a suitable surface, the present composition forms a substantially hydrophobic coating of the anionic functionalized siloxane polymer on the treated surface. These polymers effectively deposit on surfaces that have cationic sites, which are capable of forming bonds or linkages with the anionic groups of the polymer. The treated surface becomes hydrophobic due to the deposition of the anionic functionalized siloxane polymer, which then imparts a variety of end use benefits to that surface such as ease of cleaning, soil release, stain removal and prevention, conditioning, etc. The anionic functionalized siloxane polymer further acts as a carrier to deposit active agents onto the surface and to improve retention and efficacy of the active agents on the treated surface. The present compositions are useful in a variety of applications including oral care, hair and skin care, personal care, cosmetics, and fabric and hard surface cleaning and conditioning.

9 Claims, No Drawings

U.S. PATENT DOCUMENTS 6,153,567 A    11/2000  Hughes
6,379,751 B1    4/2002  Schafer et al.
6,534,072 B2 *  3/2003  Mondet et al. ............. 424/401

OTHER PUBLICATIONS

"Synthesis of Amino Acid Functional Polysiloxanes" authored by Provatas et al. and published in Polymer Preprints (American Chemical Society, Division of Polymer Chemistry) 1998, p. 546-547.*

"Adhesive Polysiloxanes with Hydrogen Bond Donors or Acceptors" authored by Teyssie et al., and published in Silicones in Coatings, 2nd Conference in the Series: High Performance Coating Materials, Brussels, Jan. 29-31, 1996, Paper 15/1-8.*

* cited by examiner

COMPOSITIONS COMPRISING ANIONIC FUNCTIONALIZED POLYORGANOSILOXANES FOR HYDROPHOBICALLY MODIFYING SURFACES AND ENHANCING DELIVERY OF ACTIVE AGENTS TO SURFACES TREATED THEREWITH

CROSS REFERENCE TO RELATED APPLICATIONS

This application claims the benefit of U.S. Provisional Application No. 60/378,997, filed May 9, 2002.

FIELD OF THE INVENTION

This invention provides compositions and methods for treating and modifying surfaces and for enhancing delivery of active agents to surfaces treated therewith, wherein the compositions comprise siloxane polymers functionalized with pendant moieties comprising two or more anionic groups, at least one anionic group being a carboxy group. When applied to a suitable surface, the present composition forms a substantially hydrophobic coating of the anionic functionalized siloxane polymer on the treated surface. These polymers effectively deposit on surfaces that have cationic sites, which are capable of forming bonds or linkages with the anionic groups of the polymer. The treated surface becomes hydrophobic due to the deposition of the anionic functionalized siloxane polymer, which then imparts a variety of end use benefits to that surface such as ease of cleaning, soil release, stain removal and prevention, conditioning, etc. The anionic functionalized siloxane polymer further acts to enhance deposition of active agents onto the surface and to improve retention and efficacy of these active agents on the treated surface. The present compositions are useful in a variety of applications including oral care, hair and skin care, personal care, cosmetics, and fabric and hard surface cleaning and conditioning.

BACKGROUND OF THE INVENTION

It is desirable to have a means to modify surfaces in order to impart properties to such surfaces including ease of cleaning; resistance to soiling, staining and adherence of bacteria and other unwanted deposits; water repellency; as well as appearance and textural benefits including whitening, glossiness, softness, smoothness and lubricity. While the art is replete with a myriad of products aimed at providing one or more of these benefits, there continues to be a search for improved means to deliver these benefits.

In particular, modifying surfaces to be hydrophobic, is advantageous in providing the aforementioned benefits. For example, hydrophobic surfaces tend to repel most soils and stains and would thus be easier to clean. Surfaces such as fabrics, ceramics, porcelain, glass and teeth can be hydrophobically modified for ease of cleaning and anti-staining benefits. A hydrophobic coating on fabrics, paper, leather, skin and hair would also provide desirable textural characteristics including softness, smoothness and lubricity.

Silicone oils including the polyalkylsiloxanes such as polydimethylsiloxanes (PDMS), because of their hydrophobic nature, have been suggested for inclusion for example in oral hygiene preparations to inhibit the adhesion of food particles, cellular debris and plaque precursors to teeth such as described in U.S. Pat. Nos. 5,032,387; 5,165,913; 5,057,308 all to Hill, et al. U.S. Pat. No. 5,422,098 to Rolla et al. discloses dentifrices comprising a liquid silicone oil, such as PDMS, and a fat-soluble antibacterial agent dissolved therein, which is described as being useful for protection of teeth against plaque formation due to a slow release of antibacterial agent into the saliva. However, PDMS polymers have not generally been used successfully for coating the teeth because of poor adhesion and retention of the PDMS on tooth surfaces. To improve the adherence of the silicone on surfaces, it has been suggested to modify the silicone by addition of functional groups such as carboxy, anhydride, polyol and amino groups. Such modified silicones have been suggested for modifying various surfaces; including fibers, textiles, leather, hair and skin, teeth, paper, plastic, wood, metal, glass, stone and concrete. For example, aminoalkyl silicones are described in U.S. Pat. Nos. 5,078,988; 5,154,915; 5,188,822; and 5,427,770, all assigned to Chesebrough-Ponds and in U.S. Pat. Nos. 6,153,567; 6,129,906 and 6,024,891, all assigned to Procter & Gamble. Carboxyl or anhydride group containing silicones are disclosed in U.S. Pat. Nos. 4,501,619; 4,563,347; 4,587,320; 4,944,978; 5,063,044 5,280,019, all assigned to Dow Corning; in U.S. Pat. No. 4,857,212 assigned to Toray Silicone; U.S. Pat. Nos. 4,701,269; 4,931,062; 5,702,490 and 6,007,801, all assigned to BASF; U.S. Pat. No. 4,658,049 assigned to Chisso; U.S. Pat. No. 4,844,888 assigned to Gillette; U.S. Pat. Nos. 5,248,783 and 5,296,625 both assigned to Siltech; U.S. Pat. Nos. 5,015,700 and 5,504,233 assigned to Wacker Chemie; JP Patent Publication No. 04/120014 and U.S. Pat. No. 5,210,251 assigned to Kao; U.S. Pat. No. 4,876,152 assigned to PPG; U.S. Pat. No. 4,342,742 assigned to L'Oreal and U.S. Pat. Nos. 5,536,304 and 5,888,491, both assigned to 3M. Dimethicone copolyols are disclosed in U.S. Pat. Nos. 5,759,523; 5,827,505; 5,856,282; 6,004,538 and 6,129,906 all assigned to Procter & Gamble.

Even with the substantial body of work in this area, there continues to be a search for substantive polymers that can be deposited onto surfaces to modify the characteristics of these surfaces thereby providing a variety of the aforementioned benefits thereon. The present invention thus provides substantive anionic functionalized siloxane polymers that modify surfaces to be hydrophobic and compositions comprising these polymers, which find utility, in a variety of applications including hair and skin care, personal care, cosmetics, fabric and hard surface cleaning and conditioning, and particularly applications for the care of teeth and other surfaces of the oral cavity.

SUMMARY OF THE INVENTION

The present invention provides compositions for use in hydrophobically modifying surfaces thereby imparting to those surfaces end use benefits including ease of cleaning, soil release, stain removal and prevention, whitening, and conditioning. The compositions comprise at least about 0.001% by weight of a carboxy functionalized siloxane polymer in a formulation that effectively deposits the polymer to surfaces containing cationic sites forming a substantive coating having prolonged retention thereon. The present polymers comprise a hydrophobic siloxane backbone having pendant moieties containing two or more anionic groups, at least one anionic group being a carboxy group. Surfaces containing cationic sites that may be treated with the present compositions include teeth and other oral cavity surfaces, hair, skin, fibers, textiles, leather, paper, plastic, wood, metal, glass, stone and concrete. For example, the compositions are useful for cleaning and whitening of natural teeth and dental prosthesis and for preventing, reducing or removing plaque, calculus and surface deposited stains on teeth. The compositions may be aqueous or non-aqueous based and may further comprise one or more active agents for treating the surface such as whitening or bleaching agents, antimicrobials, anticaries agents, enzymes, hair and skin conditioning agents, cosmetic ingredients, flavors and fragrances. Advantageously, the present polymers have the ability to act as a carrier for these active agents, and can thus act as a highly effective matrix for sustained release of the active agents to the surface where their activity is needed.

These and other features, aspects, and advantages of the present invention will become evident to those skilled in the art from the following detailed description.

DETAILED DESCRIPTION OF THE INVENTION

While the specification concludes with claims, which particularly point out and distinctly claim the invention, it is believed the present invention will be better understood from the following description.

All percentages and ratios used herein are by weight of the specific composition, and not of the overall formulation that is delivered, unless otherwise specified. All measurements are made at 25° C., unless otherwise specified.

Herein, "comprising" means that other steps and other ingredients which do not affect the end result can be added. This term encompasses the terms "consisting of" and "consisting essentially of".

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition of the present invention may be in the form of a toothpaste, dentifrice, tooth powder, oral gel, subgingival gel, mouthrinse, denture product, mouthspray, lozenge, oral tablet, or chewing gum. The oral care composition may also be incorporated onto strips or films, which are directly applied or attached to teeth or other oral surfaces.

The term "dentifrice", as used herein, means paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier" for use in oral care compositions as used herein means any safe and effective materials for use in the compositions of the present invention. Such materials include fluoride ion sources, anticalculus agents, buffers, abrasive polishing materials, peroxide sources, alkali metal bicarbonate salts, thickening materials, humectants, water, surfactants, titanium dioxide, flavor system, sweetening agents, xylitol, coloring and opacifying agents, and mixtures thereof.

Herein, the terms "tartar" and "calculus" are used interchangeably and refer to mineralized dental plaque deposits.

In accordance with the present invention, there is provided compositions comprising as essential ingredient at least one siloxane polymer functionalized with pendant moieties comprising two or more anionic groups, at least one anionic group being a carboxy group, for application to surfaces that contain cationic sites, such as teeth, ceramics, skin, fabrics, hair, glass and paper. The compositions comprise at least about 0.001% of the anionic functionalized siloxane polymer in a formulation that effectively deposits the polymer to the treated surface. The present polymers comprise a hydrophobic siloxane backbone and pendant moieties containing carboxy and other anionic groups selected from hydroxy, amino, and alkoxy and have the ability to deposit onto surfaces from aqueous-based formulations such as cleaning and detergent compositions or from essentially non-aqueous based formulations such as lotions and creams. When applied to a suitable surface, the present composition comprising the anionic functionalized siloxane polymers forms a substantially hydrophobic coating on the treated surface, the coating having prolonged retention thereon.

The anionic functionalized siloxane polymers useful in the present invention are believed to attach themselves to polar surfaces and to form a deposit thereon by electrostatic interaction, such as by complex formation between the pendant anionic groups of the polymer with cationic sites on the treated surface. For example, in the case of oral application it is believed the anionic groups will interact with calcium ions present in teeth. In the case of fabrics, the interaction may be with calcium ions or cellulose groups; in the case of hair or skin, with protein residues; in the case of glass or ceramics, with calcium and other metal ions. The anionic groups thus serve to anchor the siloxane polymer backbone onto the surface thereby modifying the surface to be hydrophobic.

Anionic functionalized polyorganosiloxanes useful in the present invention may be represented by the formula

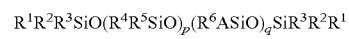

wherein $R^1$ to $R^6$, which may be identical or different, each represents a linear or branched C1–C8 alkyl or phenyl radical, preferably methyl;

A represents a carboxy group containing radical of formula

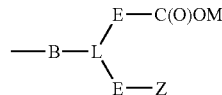

wherein B represents an alkylene residue having from 2 to 30 carbon atoms, preferably from 3 to 8 carbon atoms, optionally interrupted by up to 8 non-neighboring oxygen atoms or groups of the formula —$NR^7$—, —CO— or —C(O)—O—C(O)—, wherein $R^7$ is hydrogen or C1–C4 alkyl, L represents CR' or phenyl, wherein R' represents a hydrogen atom, an alkyl radical having from 1 to 30 carbon atoms or a carboxy group, E is nil or is an alkylene residue having from 1 to 5 carbon atoms, preferably from 1 to 3 carbon atoms, optionally substituted by one or more alkyl radicals having from 1 to 8 carbon atoms, Z represents an anionic functional group selected from hydroxy, amino, carboxy, or alkoxy, wherein when L is CR', Z is other than carboxy and when L is phenyl, the groups -E-C(O)OM and -E-Z are ortho to each other and E is nil, and M is H, a cation, or an alkyl group having from 1 to 4 carbon atoms optionally substituted with a hydroxy or alkoxy groups;

p is an average value ranging from 0 to 1000, preferably from 5 to 200; and q is an average value ranging from 1 to 100, preferably from 1 to 50.

The cation salts of the carboxy radical can be alkali metal (sodium, potassium, lithium) salts, alkaline earth metal (calcium, barium) salts, substituted or non substituted ammonium (methyl-, dimethyl-, trimethyl-, or tetramethylammonium, dimethylpiperidinium) salts or can derive from an alkanolamine (monoethanolamine, diethanolamine, triethanolamine).

In addition to the ester derivatives of the carboxy radical (M=alkyl), the present invention includes the amide derivatives.

Preferably the p/q ratio is from 1/3 to 99/1 (corresponding to 1–75% of pendant anionic groups relative to the siloxyl units), more preferably from 1/1 to 10/1.

The present anionic functionalized siloxane polymers are generally prepared starting with a hydrosilylation reaction of a polyalkylhydrogenosiloxane with an appropriate terminal olefin having reactive groups such as hydroxy, carboxy, alkoxy and acetoxy. Examples of suitable terminal olefins include allyl acetate and undecylenic acid. The product of the hydrosilylation reaction is the precursor of the pendant A moiety containing carboxy and other anionic groups. The hydrosilylation reaction is preferably carried out with the aid of an effective amount of a metal catalyst (platinum), as described for example, in U.S. Pat. Nos. 3,159,601; 3,159,662; and 3,814,730. The hydrosilylation reaction can be carried out at a temperature from 20 to 200° C., preferably from 60 to 120° C., preferably with the aid of a platinum KARSTEDT catalyst (from 1 to 300 ppm, preferably from 5 to 50 ppm by weight of Pt). When additional functionalities are required, moiety A may be suitably substituted to facilitate addition of other groups or to influence interfunctional conversions. Such chemistry on the pendant groups is performed using well-established methods and reagents known in organic chemistry.

Preferred polymers comprise one or a combination of the following pendant groups:

—(CH$_2$)$_n$—C$_6$H$_3$(COOM)$_2$
—(CH$_2$)$_n$—C$_6$H$_3$(OH)(COOM)
—(CH$_2$)$_n$—C$_6$H$_3$(OCOCH$_3$)(COOM)
—(CH$_2$)$_n$—C$_6$H$_3$(NHR)(COOM)
—(CH$_2$)$_n$—OC(O)—CHOH—CH$_2$COOM
—(CH$_2$)$_n$—OC(O)—CH$_2$—C(OH)(COOM)—CH$_2$COOM
—(CH$_2$)$_n$—OC(O)—CH(OH)—COOM
—(CH$_2$)$_n$—OC(O)—(CHOH)$_m$—CH(OH)COOM
—(CH$_2$)$_n$—C(O)—O—C(O)—CH2—CH(OH)—COOM wherein n is from 2 to 30, m is from 2 to 4 and R is H or C1–C8 alkyl.

The hydroxy groups in the above pendant groups may be acetylated or converted to amino or alkyl amino groups. In cases where possible, the hydroxy and carboxylic acid groups may exist in the form of lactones, and similarly, the dicarboxylic acids may exist as anhydrides.

Particularly preferred polymers comprise pendant anionic functional moieties that comprise at least one carboxy group and a beta hydroxy group, which has been found to result in improved deposition and retention of the polymer particularly on surfaces such as teeth that contain positively-charged calcium ions. The interaction between the polymer and the surface is electrostatic in nature in which the anionic carboxy and hydroxy groups of the pendant moieties form a complex with the positively charged calcium on the surface. This interaction becomes even stronger when two or more carboxy groups are present along with a beta hydroxy group.

Suitable polymers for use in the present invention are siloxane polymers with pendant groups derived from carboxylate compounds that are known to interact with calcium by way of complexation, hydrogen bonding and ion exchange. Examples include citric acid, malic acid, tartaric acid, salicylic acid, phthalic acid, and gluconic acid. Among preferred polymers are siloxane polymers with —(CH$_2$)$_3$—OC(O)—CHOH—CH$_2$COOH (derived from malic acid) or —(CH$_2$)$_3$—C$_6$H$_3$(COOH)$_2$ (derived from phthalic acid) pendant groups and having an average molecular weight (AMW) ranging from about 300 to about 300,000. Preferably, polymers have an average molecular weight ranging from 1000 to 100,000 and have from about 1% to 75% of pendant anionic groups relative to the siloxyl units.

In the embodiment where the anionic pendant group A in the functionalized polyorganosiloxane is derived from malic acid, the polymer is prepared by starting with a hydrosilylation reaction of a polyalkylhydrogensiloxane and allyl acetate to introduce a propyl acetate group pendant from the polysiloxane chain. The propyl acetate pendant group is then hydrolyzed and then made to undergo an esterification reaction with an excess of malic acid in a non-hydroxylic solvent. Polymers with pendant groups derived from other hydroxy carboxylates can be similarly prepared.

In another preferred embodiment, the anionic pendant group is derived from allyl phthalic anhydride. The polymer is prepared by a hydrosilylation reaction of a polyalkylhydrogensiloxane and allyl phthalic anhydride, followed by hydrolysis of the anhydride to the dicarboxylic acid.

The preferred polyalkylhydrogensiloxane for use in preparing the functionalized polymers is polydimethylhydrogensiloxane and the polymers are terminated with trimethylsilyl groups.

The anionic groups provide ready bonding/binding to cationic and charged surfaces via electrostatic interaction, hydrogen bonding, and complexation with cations. Such bonding leads to ready deposition of the polymer upon application to form a coating on the treated surface, charge interaction being the driving force, and at the same time stronger bonding leading to longer retention or durability of the coating. The polysiloxane backbone makes the surface hydrophobic, which imparts properties to the surface including water repellency, faster drying, stain repellency, ease of cleaning, soil release, softness and lubricity. Compared to non-functionalized polysiloxanes such as PDMS, the present polymers perform better not only in terms of ease of deposition and retention of the coating, but also in requiring lower levels and in being easier to formulate and emulsify with ordinary surfactants. Even more advantageously, the present polymers have the ability to act as a carrier for other active agents such as for example, teeth whitening agents including bleaches and teeth color modifying substances, antimicrobials, anticaries agents, enzymes, cosmetic ingredients, flavors and fragrances, and can thus act as a highly effective matrix for sustained release of the active agents to the surface where their activity is needed. Another important advantage of the polymer coating is substantivity or the ability to bind or adhere to a surface for a prolonged period of time. Specifically, substantivity relates to the ability of the polymer coating to be retained on the treated surface thereby acting as protective barrier to prevent active agents deposited thereon from being rapidly washed away. Substantivity is important because it allows for prolonged contact of the active agents with the surface being treated. The result is enhancement of the bleaching, antimicrobial or other active effect delivered to the surface. The present invention therefore provides surface treating compositions that deposit on the surface a substantive hydrophobic coating that is retained for a sufficient period of time to deliver a desired benefit particularly with repeated use of the composition.

In particular, with respect to bleach delivery from a daily use oral care composition such as a dentifrice or mouthrinse, the present polymers having a hydrophobic polysiloxane backbone and pendant moieties containing anionic groups are uniquely suited to facilitate delivery and retention of the bleaching agent on teeth for a period of time sufficient to provide a noticeable whitening benefit, particularly with repeated use of the compositions. Applicants have found that conventional dentifrices containing bleach are generally ineffective at providing a noticeable whitening benefit because the bleach is not retained on teeth for a long enough period. The present method of using a substantive polymer to deposit and retain the bleaching agent for a prolonged contact time with teeth thus represents a novel approach.

Notwithstanding the specific polysiloxane structures described herein, it is expected that other hydrophobic polymers suitably functionalized to deposit and adhere to teeth and to facilitate delivery and retention of bleach actives would provide the desired whitening benefit. By "suitably functionalized" is meant that the polymer contains functional groups that would interact with the tooth surface such as by complexation with calcium ions to form a substantive hydrophobic coating thereon. By forming a "substantive hydrophobic coating" on a surface is meant that the hydrophobic character of the surface is increased as measured, for example, by an increase in the water contact angle of the surface of at least about 15 degrees and the increased hydrophobic character is maintained for a period of at least about 5 minutes. For example, the water contact angle of dental enamel after treatment with a composition comprising a propylsuccinic acid functionalized siloxane polymer (AMW=1700) has been demonstrated to increase by about 20 degrees up to as much as about 50 degrees depending on a number of factors including pH, the condition of the oral environment and tooth surface characteristics.

In one aspect the present invention provides oral care compositions that deposit a hydrophobic coating on teeth or other oral surface, which coating is retained for a period of at least about 5 minutes up to about eight hours following each use of the composition. For example, oral care compositions for daily use are provided comprising in an orally acceptable carrier at least about 0.1% of an anionic functionalized siloxane polymer that deposit a hydrophobic coating on teeth, which coating is retained for a period of at least about 5 minutes up to about eight hours following each use. The present oral care compositions provide enhanced overall cleaning, inhibition of plaque, whitening, stain removal and prevention of staining of natural teeth and dental prosthesis as well as shine, smoothness and positive feel benefits to teeth. Without wishing to be limited to a particular mechanism of action, it is believed the carboxy and other anionic groups of the present functionalized siloxane polymer, react with the positively charged calcium ions present on the tooth surface forming a stable complex. The calcium/polymer complex is particularly stable when the pendant moieties contain two anionic groups that complex with divalent calcium ions resulting in the formation of 5-, 6- or 7-membered ring structures. Such complex formation is the driving force for deposition and retention of the polymer coating onto teeth. It is believed that the polymer coating on the teeth acts as a barrier to prevent staining and plaque formation. Color bodies or staining materials such as polyphenolic compounds (catechols and tannins) are constituents of various dietary products such as tea, coffee, wine, cola, and a variety of fruits and berries. Consumption of these dietary products is known to cause deposition of staining materials on teeth. When the present compositions are applied to the oral cavity such as by toothbrushing or by rinsing, a hydrophobic siloxane polymer coating is deposited onto teeth. Thus when color bodies are introduced in the oral cavity, they contact the siloxane polymer coating instead of the tooth surface, thereby preventing stain from forming on teeth. Freshly formed plaque can also be prevented from forming on teeth and the polymer coating additionally inhibits the ability of plaque to absorb colored components from ingested products such as tea, beer, red wines, etc. and form stain on teeth.

Further, the present anionic functionalized polymers have the ability to act as a carrier for oral care actives such as bleaches and other teeth whitening agents, antimicrobials, fluoride, desensitizing agents, and flavors and to facilitate deposition and retention of these actives onto the oral surfaces where they can perform their intended function. It is believed the polymer coating acts as a protective barrier that retains the oral care active in close proximity to the oral surface thereby ensuring that the activity such as bleaching or antimicrobial effect lasts longer. Effective bleaching will remove stains and lead to whiter teeth. Enhanced retention of antimicrobials on the oral surfaces will result in reducing the oral microorganisms that are causative agents for, or associated with, various dental diseases, including gingivitis, and periodontal disease and dental plaque.

Accordingly in a further aspect of the invention, there is provided a composition for use in overall cleaning, whitening, removing stain and preventing stain build-up on human teeth and dental prosthesis comprising the combination of at least about 0.1% of the present anionic-functionalized siloxane polymer and from about 0.1% to about 20.0% teeth whitening agent, preferably from about 1% to about 10% teeth whitening agent in an orally acceptable carrier. The polymer is incorporated in the present dentifrice, rinse, chewing gum and the like compositions at about 0.1% to about 20% by weight, preferably from about 0.5% to about 5% by weight. Greater amounts up to about 80% may be used for oral gels such as paint-on or leave-on gels or for denture adhesives.

Teeth whitening actives that may be used in the oral care compositions of the present invention include bleaching or oxidizing agents such as peroxides, perborates, percarbonates, peroxyacids, persulfates, metal chlorites, and combinations thereof. Suitable peroxide compounds include hydrogen peroxide, urea peroxide, calcium peroxide, and mixtures thereof. A preferred percarbonate is sodium percarbonate. Other suitable whitening agents include potassium, ammonium, sodium and lithium persulfates and perborate mono- and tetrahydrates, and sodium pyrophosphate peroxyhydrate. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide.

In addition to bleaching agents as teeth whitening agents, teeth color modifying substances may be considered among the oral care actives useful in the present invention. These substances are suitable for modifying the color of the teeth to satisfy the consumer. These substances comprise particles that when applied on the tooth surface, modify that surface in terms of absorption and/or reflection of light. Such particles provide an appearance benefit when a film containing such particles is applied over the surfaces of a tooth or teeth.

Particles most useful in the present invention include pigments and colorants routinely used in the cosmetic arts. There are no specific limitations as to the pigment and, or colorant used in the present composition other than the limitation of the effect it has on the light source upon the teeth surfaces. Pigments and colorants include inorganic white pigments, inorganic colored pigments, pearling agents, filler powders and the like; see Japanese Published Patent Application Kokai No. 9-100215, published Apr. 15, 1997. Specific examples are selected from the group consisting of talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Most preferred are those selected from the group consisting of titanium dioxide, bismuth oxychloride, zinc oxide and mixtures thereof. Pigments that are generally recognized as safe, and are listed in *C.T.F.A. Cosmetic Ingredient Handbook*, 3rd Ed., Cosmetic and Fragrance Assn., Inc., Washington D.C. (1982).

The pigments are typically used as opacifiers and colorants. These pigments can be used as treated particles, or as the raw pigments themselves. Typical pigment levels are selected for the particular impact that is desired by the consumer. For example, for teeth that are particularly dark or stained one would typically use pigments in sufficient amount to lighten the teeth. On the other hand, where individual teeth or spots on the teeth are lighter than other teeth, pigments to darken the teeth may be useful. The levels of pigments and colorants are generally used in the range of about 0.05% to about 20%, preferably from about 0.10% to about 15% and most preferably from about 0.25% to about 10% of the composition.

The present oral care compositions may also include other active agents, such as antimicrobial agents. Included among such agents are water insoluble non-cationic antimicrobial agents such as halogenated diphenyl ethers, phenolic compounds including phenol and its homologs, mono and polyalkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquamide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey. Other antimicrobials such as copper bisglycinate, copper glycinate, zinc citrate, and zinc lactate may also be included. Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranases, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to anti-microbial properties. Such agents are disclosed in U.S. Pat. No. 2,946,725, Jul. 26, 1960, to Norris et al. and in U.S. Pat. No. 4,051,234, Sep. 27, 1977 to Gieske et al. Other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, issued May 14, 1991, and U.S. Pat. No. 4,894,220, issued Jan. 16, 1990 to Nabi et al. These agents, which provide anti-plaque benefits, may be present at levels of from about 0.01% to about 5.0%, by weight of the dentifrice composition.

The oral care composition of the present invention may be in the form of a dentifrice, toothpaste, tooth powder, topical oral gel, mouthrinse, denture product, mouthspray, lozenge, oral tablet, or chewing gum. The oral care composition may also be incorporated onto strips or films for direct application or attachment to oral surfaces.

The present oral care compositions in aqueous form will optimally have a pH ranging from about 4.0 to about 10.0. Preferred pH of the oral care compositions is from about 5.0 to about 9.0.

In addition to the components described above, the present oral care compositions may comprise an orally acceptable carrier, which comprises one or more compatible solid or liquid filler diluents or encapsulating substances suitable for topical oral administration. By "compatible," as used herein, is meant that the components of the composition are capable of being commingled without interaction in a manner which would substantially reduce the composition's stability and/or efficacy.

The carriers or excipients can include the usual and conventional components of dentifrices (including non-abrasive gels and gels for subgingival application), mouth rinses, mouth sprays, chewing gums, and lozenges (including breath mints). The choice of a carrier to be used is basically determined by the way the composition is to be introduced into the oral cavity. Carriers suitable for the preparation of compositions of the present invention are well known in the art. Their selection will depend on secondary considerations like taste, cost, and shelf stability, etc. Types of carriers or oral care excipients, which may be used in compositions of the present invention include but are not limited to water, solvents, abrasives, surfactants, anticalculus agents, chelating agents, fluoride sources, opacifiers and colorants, humectants, thickening agents, and flavoring and sweetening agents. For example, toothpaste and mouth rinse carriers are disclosed in e.g., U.S. Pat. No. 3,988,433 to Benedict. Lozenge carrier (e.g., a candy base) and chewing gum carrier (comprising e.g., gum base, flavoring and sweetening agents) are disclosed in, e.g., U.S. Pat. No. 4,083,955, to Grabenstetter et al. For subgingival gels (for delivery of actives into the periodontal pockets or around the periodontal pockets), a "subgingival gel carrier" is chosen as disclosed in, e.g., U.S. Pat. No. 5,198,220, issued Mar. 30, 1993 and U.S. Pat. No. 5,242,910, issued Sep. 7, 1993, both to Damani. Other useful carriers include biphasic dentifrice formulations such as those disclosed in U.S. Pat. No. 5,213,790, issued May 23, 1993, U.S. Pat. No. 5,145,666, issued Sep. 8, 1992, and U.S. Pat. No. 5,281,410 issued Jan. 25, 1994 all to Lukacovic et al. and in U.S. Pat. Nos. 4,849,213 and 4,528,180 to Schaeffer.

The oral care compositions of the present invention may be in the form of non-abrasive gels, including subgingival gels, which may be aqueous or non-aqueous. Aqueous gels generally include a thickening agent (from about 0.1% to about 20%), a humectant (from about 10% to about 55%), a flavoring agent (from about 0.04% to about 2%), a sweetening agent (from about 0.1% to about 3%), a coloring agent (from about 0.01% to about 0.5%), and the balance water. The compositions may comprise an anticaries agent (from about 0.05% to about 0.3% as fluoride ion), and an anticalculus agent (from about 0.1% to about 13%).

Compositions of the subject invention may also be in the form of dentifrices, such as toothpastes, tooth gels and tooth powders. Components of such toothpaste and tooth gels generally include one or more of a dental abrasive (from about 5% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the subject invention are mouthwashes, including mouth sprays. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion), and an anticalculus agent (from about 0.1% to about 3%).

Other preferred compositions of the subject invention are dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 50% to about 99%), a flavoring agent (from about 0.4% to about 2%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in commonly-assigned WO 95/33446 and WO 95/11671; U.S. Pat. No. 4,642,903; U.S. Pat. No. 4,946,684; U.S. Pat. No. 4,305,502; U.S. Pat. No. 4,371,516; U.S. Pat. No. 5,188,825; U.S. Pat. No. 5,215,756; U.S. Pat. No. 5,298,261; U.S. Pat. No. 3,882,228; U.S. Pat. No. 4,687,662; U.S. Pat. No. 4,642,903.

Lozenges include discoid-shaped solids comprising a therapeutic agent in a flavored base.

The base may be a hard sugar candy, glycerinated gelatin or combination of sugar with sufficient mucilage to give it form. These dosage forms are generally described in Remington: *The Science and Practice of Pharmacy*, $19^{th}$ Ed., Vol. II, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, Peterson et al., issued Dec. 6, 1994.

In still another aspect, the invention provides a dental implement impregnated with the present composition. The dental implement comprises an implement for contact with teeth and other tissues in the oral cavity, said implement being impregnated with a composition comprising the present anionic functionalized siloxane polymer. The dental implement can be impregnated fibers including dental floss or tape, chips or strips and polymer fibers.

The pH of the present compositions is preferably adjusted through the use of buffering agents. Buffering agents, as used herein, refer to agents that can be used to adjust the pH of the compositions to a range of about pH 4.0 to about pH 10.0. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions. The pH of dentifrice compositions is measured from a 3:1 aqueous slurry of dentifrice, e.g., 3 parts water to 1 part dentifrice.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits.

Poloxamers may also be employed in the present compositions. A poloxamer is classified as a nonionic surfactant. It may also function as an emulsifying agent, binder, stabilizer, and other related functions. Poloxamers are difunctional block-polymers terminating in primary hydroxyl groups with molecular weights ranging from 1,000 to above 15,000. Poloxamers are sold under the tradenames of Pluronic and Pluraflo by BASF. Preferred poloxamers for this invention is Poloxamer 407 and Pluraflo L4370.

Other emulsifying agents that may be used in the present compositions include polymeric emulsifiers such as the Pemulen® series available from B. F. Goodrich, and which are predominantly high molecular weight polyacrylic acid polymers useful as emulsifiers for hydrophobic substances.

The present invention also relates to methods for cleaning and polishing teeth, reducing and preventing the incidence of caries, gingivitis and of stain, plaque and calculus on dental enamel, and providing shine, smoothness and positive feel benefits to teeth.

A method of use herein comprises contacting a subject's dental enamel surfaces and oral mucosa with the oral care compositions according to the present invention. Methods of use may be by brushing with a dentifrice, rinsing with a dentifrice slurry or mouthrinse, or chewing a gum product. Other methods include contacting the topical oral gel, mouthspray, or other form such as strips or films with the subject's teeth and oral mucosa. The composition may be applied directly to the teeth, gums, or other oral surface with a brush, a pen applicator, a doe's foot applicator, or the like, or even with the fingers. The subject may be any person or other animal whose tooth surface contacts the oral care composition. By "other animal' is meant to include household pets or other domestic animals, or animals kept in captivity. For example, a method of use may include brushing a dog's teeth with one of the dentifrice compositions. Another example would include the rinsing of a cat's mouth with an oral care composition for a sufficient amount of time to see a benefit. Pet care products such as chews and toys may be formulated to contain the present oral care compositions. The composition including the present copolymer is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

In a further aspect of the present invention, compositions are provided that are useful for hair, skin, cosmetic and personal care applications and for home care applications such as for cleaning, conditioning and disinfecting fabrics and hard surfaces. The compositions comprise at least about 0.001% of the present anionic-functionalized siloxane polymer which function to hydrophobically modify the treated surface and to enhance delivery to that surface of one or more active agents contained in the compositions.

One embodiment provides antimicrobial skin cleansing compositions having improved antibacterial, antiviral, and/or antifungal activity as well as improved mildness to the skin, wherein the compositions comprise at least about 0.1% of the present anionic-functionalized siloxane polymer, from about 0.001% to about 5.0% by weight of an antimicrobial active and from about 0.05% to about 10% by weight of a surfactant selected from the group consisting of anionic surfactants, amphoteric surfactants, or a combination of anionic and amphoteric surfactants. The cleansing compositions of the present invention generally have a pH in the range of about 2.0 to about 5.5. The cleansing compositions described herein additionally comprise an aqueous carrier. The term "aqueous carrier" refers to any material consisting essentially of, or predominantly of water, water soluble alcohol(s) such as ethanol, propanol or isopropanol, and mixtures thereof. The aqueous carrier can optionally contain one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art. Antimicrobial skin cleansing compositions are disclosed, for example, in commonly assigned copending application U.S. Ser. No. 09/738,365, filed Dec. 15, 2000 and published as US 2002/0002124A1.

Optional ingredients to enhance the mildness to the skin may also be added. These ingredients include cationic and nonionic polymers, co-surfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. Co-surfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. Another group of mildness enhancers are lipid skin moisturizing agents, which provide a moisturizing benefit to the user of the cleansing composition when the lipophilic skin moisturizing agent is deposited to the user's skin.

The compositions may also comprise a wide range of additional optional ingredients. The *CTFA International Cosmetic Ingredient Dictionary*, Sixth Edition, 1995, describes a wide variety of nonlimiting cosmetic and pharmaceutical ingredients commonly used in the skin care industry, which are suitable for use in the compositions of the present invention. Nonlimiting examples of functional classes of ingredients include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

The antimicrobial cleansing compositions of the present invention are highly efficacious for providing improved germ reduction on the skin, are mild to the skin and can be used without additional available water.

The antimicrobial cleansing compositions of the present invention can also be used on non-skin surfaces, such as household surfaces, e.g., countertops, kitchen surfaces, food preparing surfaces (cutting boards, dishes, pots and pans, and the like); major household appliances, e.g., refrigerators, freezers, washing machines, automatic dryers, ovens, microwave ovens, dishwashers; cabinets; walls; floors; bathroom surfaces, shower curtains; garbage cans and/or recycling bins, and the like.

Further, the present antimicrobial cleansing compositions can be incorporated into an insoluble substrate for application to the skin or non-skin surface such as in the form of a treated wipe. Suitable water insoluble substrate materials and methods of manufacture are described in Riedel, "Nonwoven Bonding Methods and Materials," *Nonwoven World* (1987); *The Encyclopedia Americana*, vol. 11, pp. 147–153, vol. 21, pp. 376–383, and vol. 26, pp. 566–581 (1984); U.S. Pat. No. 3,485,786 to Evans, issued Dec. 23, 1969; U.S. Pat. No. 2,862,251, to Kalwarres; U.S. Pat. No. 3,025,585, Kalwarres; U.S. Pat. No. 4,891,227, to Thaman et al., issued Jan. 2, 1990; and U.S. Pat. No. 4,891,228 and U.S. Pat. No. 5,686,088 to Mitra et al., issued Nov. 11, 1997; U.S. Pat. No. 5,674,591; James et al; issued Oct. 7, 1997.

Nonwoven substrates made from synthetic materials useful in the present invention can also be obtained from a wide variety of commercial sources. Nonlimiting examples of suitable nonwoven layer materials useful herein include PGI Miratec Herringbone, a patterned hydroentangled material containing about 30% rayon and 70% polyester, and having a basis weight of about 56 grams per square yard (gsy), available from PGI/Chicopee, Dayton N.J.; PGI Miratec Starburst, a patterned hydroentangled material containing about 30% rayon and 70% polyester, and having a basis weight of about 56 grams per square yard (gsy), available from PGI/Chicopee, Dayton N.J.; Novonet$^R$ 149–616, a thermo-bonded grid patterned material containing about 100% polypropylene, and having a basis weight of about 50 gsy, available from Veratec, Inc., Walpole, Mass.; Novonet$^R$ 149–801, a thermo-bonded grid patterned material containing about 69% rayon, about 25% polypropylene, and about 6% cotton, and having a basis weight of about 75 gsy, available from Veratec, Inc. Walpole, Mass.; Novonet$^R$ 149–191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex$^R$ 149–801, a nubbed, apertured hydroentangled material, containing about 100% polyester, and having a basis weight of about 70 gsy, available from Veratec, Inc. Walpole, Mass.; Keybak$^R$ 951V, a dry formed apertured material, containing about 75% rayon, about 25% acrylic fibers, and having a basis weight of about 43 gsy, available from PGI/Chicopee, Dayton, N.J.; Keybak$^R$ 1368, an apertured material, containing about 75% rayon, about 25% polyester, and having a basis weight of about 39 gsy, available from PGI/Chicopee, Dayton, N.J.; Duralace$^R$ 1236, an apertured, hydroentangled material, containing about 100% rayon, and having a basis weight from about 40 gsy to about 115 gsy, available from PGI/Chicopee, Dayton, N.J.; Duralace$^R$ 5904, an apertured, hydroentangled material, containing about 100% polyester, and having a basis weight from about 40 gsy to about 115 gsy, available from PGI/Chicopee, Dayton, N.J.; Sontara 8877, an apertured hydroentangled material, containing about 50% Nylon and about 50% Pulp, and having a basis weight of about 68 gsm, available from Dupont Chemical Corp.

Alternatively, the water insoluble substrate can be a polymeric mesh sponge such as described in U.S. Pat. No. 5,650,384. The polymeric sponge comprises a plurality of plies of an extruded tubular netting mesh prepared from a strong flexible polymer, such as addition polymers of olefin monomers and polyamides of polycarboxylic acids. Although these polymeric sponges are designed to be used in conjunction with a liquid cleanser, these types of sponges can be used as the water insoluble substrate in the present invention.

Other skin care compositions that can be formulated using the present anionic functionalized siloxane polymers include lotions of the solid or semisolid type at 20° C., i.e. at ambient temperatures such as described in commonly assigned U.S. Pat. No. 5,635,191 and U.S. Pat. No. 5,643,588. By "semisolid" is meant that the lotion composition has a rheology typical of pseudoplastic or plastic fluids. When no shear is applied, the lotion compositions can have the appearance of a semi-solid but can be made to flow as the shear rate is increased. This is due to the fact that, while the lotion composition contains primarily solid components, it also includes some minor liquid components. The lotion compositions are useful for direct application to skin and for application to the outer surface of topsheets for disposable absorbent articles such as diapers. The lotion compositions applied to the topsheets are transferable to the disposable article wearer's skin by normal contact, wearer motion, and/or body heat. The lotions effectively deposit a coating on the skin of the wearer, which importantly reduces the contact of skin with wetness and other excretions and facilitates clean up.

The solid or semisolid lotion compositions of the present invention comprise: (1) emollient(s); (2) immobilizing agent (s) for the emollient; (3) optionally hydrophilic surfactant(s); and (4) other optional components. The present anionic functionalized siloxane polymers are suitable as the emollient or in combination with other emollients. As used herein, an emollient is a material that softens, soothes, supples, coats, lubricates, moisturizes, or cleanses the skin. An emollient typically accomplishes several of these objectives such as soothing, moisturizing, and lubricating the skin. Preferred emollients have either a plastic or fluid consistency at 20° C., i.e., at ambient temperatures. This particular emollient consistency allows the lotion composition to impart a soft, lubricious, lotion-like feel. Other emollients useful in the present invention can be petroleum-based, fatty acid ester type, alkyl ethoxylate type, fatty acid ester ethoxylates, fatty alcohol type, polysiloxane type, or mixtures of these emollients. Petrolatum and mineral oil are examples of preferred emollients for use in combination with the anionic functionalized polysiloxane for lotion compositions of the present invention. A key component of the lotion compositions is an agent capable of immobilizing the emollient on the topsheet to which the lotion composition is applied. Because the emollient in the composition has a plastic or fluid consistency at 20° C., it tends to flow or migrate, even when subjected to modest shear. When applied to a diaper topsheet for instance, especially in a melted or molten state, the emollient will not remain primarily on the surface of the topsheet. Instead, the emollient will tend to migrate and flow into the interior of the diaper. The immobilizing agent counteracts this tendency of the emollient to migrate or flow by keeping the emollient primarily localized on the surface of the diaper topsheet to which the lotion composition is applied. Suitable immobilizing agents for the present invention can comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof.

In preparing lotioned topsheets, the lotion composition is applied to the outer surface (i.e., body facing surface) of the topsheet. Any of a variety of application methods that evenly distribute lubricious materials having a molten or liquid consistency can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the outer surface of the topsheet. The lotioned topsheets are also useful in training pants. The term "training pants", as used herein, refers to disposable garments having fixed sides and leg openings. Another disposable absorbent article for which the lotioned topsheets of the present invention are useful are incontinence articles. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons.

A further embodiment of the present invention provides hair care compositions such as shampoos having anti-dandruff and conditioning benefits. The compositions comprise by weight of the composition, at least about 0.1% of the present anionic-functionalized siloxane polymer, from about 5% to about 50% of a surfactant component selected from the group consisting of anionic surfactants, amphoteric surfactants, or a combination of anionic and amphoteric or zwitterionic surfactants where the amphoteric surfactants are anionic or zwitterionic at the pH of the composition and from about 0.1% to about 4%, preferably from about 0.1% to about 3%, most preferably from about 0.3% to about 2%, of an anti-dandruff agent suitable for application to the hair or skin. The anti-dandruff agent provides the shampoo compositions with anti-microbial activity. The anti-dandruff agent may be particulate or soluble. Suitable, non-limiting examples of particulate anti-dandruff agents include: pyridinethione salts, selenium sulfide, particulate sulfur, and mixtures thereof. Preferred are pyridinethione salts. A suitable, non-limiting example of a soluble anti-dandruff agents is ketoconazole. Such anti-dandruff agent should be physically and chemically compatible with the essential components of the composition, and should not otherwise unduly impair product stability, aesthetics or performance. The shampoo compositions of the present invention are typically liquids, which preferably, are pourable at room temperature. The compositions preferably comprise an aqueous carrier, i.e., water, which will generally be present at a level of about 20% to about 95% by weight of the composition, preferably from about 50 to about 94%, more preferably from about 60% to about 85% by weight, for pourable, liquid formulations.

The present shampoo compositions may also comprise a variety of non-essential, optional shampoo components suitable for rendering such compositions more cosmetically or aesthetically acceptable or to provide them with additional usage benefits, provided that the optional components are physically and chemically compatible with the essential component described herein, or do not otherwise unduly impair product stability, aesthetics or performance. A variety of such ingredients are well-known to those skilled in the art, and these include without limiting the invention thereto: pearlescent aids, such as coated mica, ethylene glycol distearate; opacifiers, such as $TiO_2$; preservatives, such as benzyl alcohol, 1,3-bis(hydroxymethyl)-5,5-dimethyl-2,3-imidazolidinedione (e.g., Glydant®, Glyco, Inc., Greenwich, Conn., USA), methylchloroisothiazolinone (e.g., Kathon®, Rohm & Haas Co., Philadelphia, Pa., USA), methyl paraben, propyl paraben, and imidazolidinyl urea; fatty alcohols, such as cetearyl alcohol, cetyl alcohol, and stearyl alcohol; sodium chloride; ammonium chloride; sodium sulfate; ethyl alcohol; pH adjusting aids, such as citric acid, sodium citrate, succinic acid, phosphoric acid, monosodium phosphate, disodium phosphate, sodium hydroxide, and sodium carbonate; coloring agents or dyes; perfumes; and sequestering agents, such as disodium ethylenediamine tetraacetate, organic solvents or diluents, foam boosters, additional surfactants or cosurfactants (nonionic, cationic, zwitterionic), pediculocides, preservatives, proteins, skin active agents, suspending agents, styling polymer, sunscreens, thickeners, vitamins and viscosity adjusting agents.

The shampoo compositions of the present invention can be prepared by using various formulation and mixing techniques or methods known in the art for preparing surfactant or conditioning compositions, or other similar compositions such as disclosed in commonly assigned WO 00/66080, WO 00/66081 and WO 00/66072.

In a further embodiment of the present invention, a laundry or cleaning detergent composition is provided. The laundry or cleaning composition comprises at least about 0.1% of the present anionic-functionalized siloxane polymer and up to about 99.9% by weight of the composition of laundry ingredients such as detersive surfactants, builders, bleaching agents, enzymes, soil release polymers, dye transfer inhibitors, fillers and mixtures thereof. Preferably, the composition includes at least one detersive surfactant and at least one builder. Laundry compositions can be suitably prepared by any process chosen by the formulator, non-limiting examples of which are described in U.S. Pat. No. 5,691,297 to Nassano et al., issued Nov. 11, 1997; U.S. Pat. No. 5,574,005 to Welch et al., issued Nov. 12, 1996; U.S. Pat. No. 5,569,645 to Dinniwell et al., issued Oct. 29, 1996; U.S. Pat. No. 5,565,422 to Del Greco et al., issued Oct. 15, 1996; U.S. Pat. No. 5,516,448 to Capeci et al., issued May 14, 1996; U.S. Pat. No. 5,489,392 to Capeci et al., issued Feb. 6, 1996; and U.S. Pat. No. 5,486,303 to Capeci et al., issued Jan. 23, 1996.

Yet another embodiment of the present invention provides detergent compositions intended for use on hard surfaces, e.g., metallic, wood and vitreous surfaces, and comprising at least about 0.001% of the present anionic-functionalized siloxane polymer and up to about 99.999% by weight of the composition of cleaning ingredients such as detersive surfactants, builders, bleaching agents, enzymes, fillers and mixtures thereof. More particularly, the inclusion of the herein described anionic-functionalized siloxane polymer in detergent compositions provides soil release benefits to surfaces washed with such compositions. It has been discovered that a very thin coating of the present anionic-functionalized siloxane polymer can be deposited from a detergent composition to surfaces containing cationic sites. The coating is responsible for imparting the soil release benefits to the surface. That is, a hard surface having on it the polymeric coating may be soiled; however, the soil is not tenaciously bound to the surface by virtue of the coating and for this reason is easily washed away.

As examples of the present hard surface detergent compositions may be mentioned the following: automatic dishwasher detergents intended for home use, commercial dishwasher detergents, light duty liquid detergents, car wash detergents, rinse aids, window cleaners, toilet bowl cleaners, oven cleaners and floor cleaners, which can be prepared by using various formulation and mixing techniques or methods known in the art such as disclosed in U.S. Pat. No. 4,005,082 to Heckert et al., issued Jan. 25, 1977; U.S. Pat. No. 5,703,033 to Sherry et al., issued Dec. 30, 1997; and WO 96/34933, published Nov. 7, 1996. The previous listing is merely illustrative and is in no way limiting. The compositions may be used on any hard surface where a soil release benefit is desired. Examples of such surfaces are cooking utensils (e.g., metallic pots, pans and skillets), tableware (e.g., china, glasses, ceramic ware, and flatware), oven walls, automobiles, windows, porcelain surfaces (e.g., bathtubs, sinks and toilet bowls), and floor surfaces and countertops (e.g., polyurethane, enamel, ceramic, polyvinyl chloride, Formica, parquet, and the like).

The present hard surface cleaning compositions typically comprise water-soluble organic detersive surfactants selected from the group consisting of nonionic surfactants, zwitterionic surfactants, ampholytic surfactants and mixtures thereof. U.S. Pat. No. 3,579,454 issued May 18, 1971 to Everett J. Collier, describes suitable detergents which fall within the above listed classes.

Rinse aids are intended for use in automatic dishwashing machines used either in the home or in commercial establishments. At the end of the cleaning cycle, it is desirable that the rinse water which is sprayed onto tableware and cooking utensils drain uniformly. Such uniform draining assures that spots of water do not remain behind. Invariably the water will contain dissolved substances, which will leave behind a residue when dried. The inclusion of a rinse aid in the final rinse step insures that very little water is left behind on the dishes. The rinse aids of this invention comprise from 0.01% to 10%, preferably 0.1% to 5% of the present anionic-functionalized siloxane polymer; from 5% to 99.9%, preferably 10% to 50% of the water-soluble organic nonionic detergent; and the balance water. Optionally from 1% to 30%, preferably 5% to 10% of a sequestering agent, e.g. phosphoric, glycolic, tartaric, succinic, citric, lactic, fumaric, or gluconic acid is included in the composition.

A composition intended for use in automatic car washes comprises essentially from 0.01% to 10%, preferably 0.1% to 2% of the present anionic-functionalized siloxane polymer; from 20% to 35%, preferably 23% to 28% of the water-soluble nonionic, zwitterionic, and/or ampholytic organic detergent; and the balance water. Optionally, from 1% to 10%, preferably 1% to 3% of magnesium sulfate is included in the composition.

Light duty liquid detergent compositions are used for hand washing of cooking utensils and tableware. Such compositions comprise from 0.01% to 10%, preferably 0.1% to 2% of the present anionic-functionalized siloxane polymer; from 10% to 90%, preferably 20% to 40% of the water-soluble nonionic, zwitterionic, and/or ampholytic detergent; and the balance water. Optionally, an electrolyte such as potassium chloride or sodium chloride is included in the composition at a level of from 0.5% to 5%, preferably 1% to 2%. Other optional components include a hydrotrope, e.g. toluene sulfonate, cumene sulfonate or xylene sulfonate at a level of from 1% to 20%, preferably 2% to 5%, and a lower alcohol, e.g. a C1–4 alcohol at a level of from 1% to 20%, preferably 3% to 10%.

A detergent composition intended for use in an automatic dishwashing machine in the home is also encompassed by this invention. Such compositions comprise from 0.01% to 5%, preferably 0.1% to 2% of the present anionic-functionalized siloxane polymer; from 0.1% to 15%, preferably 1% to 5% of the water-soluble nonionic detergent; from 5% to 60%, preferably 30% to 50% of a water-soluble organic or inorganic alkaline builder salt; and the balance inert filler salts. Suitable water-soluble organic and inorganic alkaline builder salts include the following: sodium tripolyphosphate, sodium citrate, sodium carbonate and sodium nitrilotriacetate. Sodium sulfate and sodium chloride are suitable inert filler salts normally included in detergent compositions of this type. These compositions can additionally contain from 7% to 35%, preferably 10% to 20%, of an alkali metal silicate. The composition can optionally also contain a bleach in an amount sufficient to give the product an available chlorine content of from 0.5% to 10%, preferably 1% to 5%. Any suitable chlorine yielding bleach can be used. Examples include: chlorinated trisodium phosphate, dichlorocyanuric acid; salts of chlorine substituted cyanuric acid; 1,3-dichloro-5,5-dimethylhydantoin; paratoluene sulfodichloroamide; trichloromelamine; N-chlorosucinimide; N,N'-dichloroazodicarbonamide; N-chloroacetyl urea; N,N'-dichlorobiuret; chlorinated dicyandiamide; sodium hypochlorite; calcium hypochlorite; and lithium hypochlorite.

A commercial dishwashing composition comprises from 0.01% to 5%, preferably 0.1% to 2% of the present anionic-functionalized siloxane polymer; from 0.1% to 15%, preferably 1% to 5% of a water-soluble nonionic detergent; from 5% to 60%, preferably 30% to 50% of a water-soluble organic or inorganic alkaline builder salt; from 10% to 40%, preferably 10% to 30% of an alkali metal base; and the balance inert filler salts. Suitable water-soluble organic or inorganic alkaline builder salts are described above in connection with the automatic dishwashing detergent composition. Examples of alkali metal bases are sodium hydroxide and potassium hydroxide. An alkali metal silicate or a chlorine bleach as described above in connection with the automatic dishwashing detergent composition can be added herein at the same levels.

Glass cleaner compositions contain from 0.001% to 5%, preferably 0.002% to 1% of the present anionic-functionalized siloxane polymer. The remainder of the glass cleaner composition comprises from 0.1% to 5%, preferably 0.5% to 3% of the water-soluble nonionic, zwitterionic, and/or ampholytic organic detergent and the balance an organic inert solvent or solvent/water mixture. Suitable organic inert solvents include the following: methanol, ethanol, isopropanol, acetone and methyl ethyl ketone.

Detergent compositions intended for the cleaning of hard surfaces such as ovens comprise from 0.002% to 5%, preferably 0.01% to 1% of the present anionic-functionalized siloxane polymer, from 0.1% to 10%, preferably 1% to 5% of the water-soluble nonionic, zwitterionic, and/or ampholytic organic detergent; from 50% to 95%, preferably 50% to 75% of a water-insoluble abrasive; and the balance inert filler salts. Suitable abrasives include the following: quartz, pumicite pumice, talc, silica sand, calcium carbonate, china clay, zirconium silicate, bentonite, diatomaceous earth, whiting, feldspar, and aluminum oxide.

The compositions of this invention are also useful as an in-tank toilet bowl cleaner. Such compositions comprise from 0.01% to 10%, preferably 0.5% to 2% of the present anionic-functionalized siloxane polymer; from 0.1% to 5%, preferably 0.5% to 2% of sodium bisulfate; from 0.1% to 20%, preferably 1% to 15% of a lower, i.e. C1–4 alcohol; from 0.5% to 20%, preferably 1% to 15% of the water-soluble organic nonionic, zwitterionic or ampholytic detergent or mixtures thereof; and the balance water, other adjunct ingredients and carriers.

Hard surface cleaning compositions for use in cleaning floors and countertops typically comprise from 0.01% to 5%, preferably 0.1% to 2% of the present anionic-functionalized siloxane polymer; from 0.1% to 15%, preferably 0.5% to 5% of a water-soluble nonionic surfactant; preferably from at least 0.1%, more preferably at least 0.5% by weight, of 2-N-propylheptyl sulfosuccinamate, and other adjunct ingredients and carriers. Examples of adjunct ingredients are buffers, builders, chelants, filler salts, dispersants, enzymes, enzyme boosters, perfumes, thickeners, clays, water, solvents, other detersive surfactants, and mixtures thereof. This list is not meant to be totally inclusive or exclusive of materials that are compatible for use in the present invention. The present hard surface cleaners can be used full strength (neat) or in diluted form. When used directly, the hard surface cleaners can be sprayed right onto the surface, poured onto a sponge or cloth or applied via an attached applicator. When used in diluted form, the cleaner may be poured into a bucket or other container containing water.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope. All percentages used herein are by weight of the composition unless otherwise indicated.

Example 1

Topical Oral Gels

Topical oral gels according to the present invention are shown below. These compositions are made using conventional methods.

Dentifrice Compositions

Dentifrice compositions according to the present invention are shown below. These compositions are made using conventional methods.

| Components | 1A | 1B | 1C | 1D | 1E | 1F | 1G |
|---|---|---|---|---|---|---|---|
| Flavor | 0.700 | 0.700 | 0.500 | 0.500 | 0.500 | 0.500 | 0.500 |
| Saccharin | 0.200 | 0.200 | 0.100 | 0.100 | 0.100 | 0.100 | 0.100 |
| Polysiloxane Functionalized with Malic Acid | 3.000 | 3.000 | 70.000 | | | 80.000 | |
| Polysiloxane Functionalized with Phthalic Acid | | | | 75.000 | 66.000 | | 75.00 |
| Urea Peroxide | 10.000 | | 20.000 | 15.000 | 15.000 | | |
| Triclosan | | | | | | 0.300 | |
| Cetyl Pyridinium Chloride | | | | | | | 1.00 |
| Pemulen TR1 | 1.000 | 1.000 | | | | | |
| Dibasic Na Phosphate | 0.200 | 0.200 | | | | | |
| Poloxamer 407 | 9.000 | 10.500 | | | | | |
| Pluraflo L4370 | QS | QS | | | | | |
| PEG 600 | | | QS | QS | QS | QS | QS |

Example 2

| Components | 2A | 2B | 2C | 2D | 2E | 2F | 2G | 2H |
|---|---|---|---|---|---|---|---|---|
| Color FD&C Blue #1 | 0.500 | 0.500 | 0.500 | 0.500 | 0.500 | 0.500 | 0.500 | 0.500 |
| Carbomer 956 | 0.300 | 0.300 | 0.300 | 0.300 | 0.300 | 0.300 | 0.300 | 0.300 |
| Flavor | 1.000 | 1.000 | 1.000 | 1.000 | 1.000 | 1.000 | 1.000 | 1.000 |
| Saccharin | 0.300 | 0.300 | 0.300 | 0.300 | 0.300 | 0.300 | 0.300 | 0.300 |
| Glycerin | | | | 40.000 | 33.000 | | | 36.000 |
| Sorbitol | 40.000 | 40.000 | 40.000 | | | 40.000 | 40.000 | |

-continued

| Components | 2A | 2B | 2C | 2D | 2E | 2F | 2G | 2H |
|---|---|---|---|---|---|---|---|---|
| Sodium Phosphate (MSP) | 0.600 | 0.600 | 0.600 | 0.600 | 0.600 | 0.600 | 0.600 | 0.600 |
| Trisodium Phosphate (TSP) | 1.450 | 1.450 | 1.450 | 1.450 | 1.450 | 1.450 | 1.450 | 1.450 |
| Xanthan Gum | 0.450 | 0.450 | 0.450 | 0.450 | 0.450 | 0.450 | 0.450 | 0.450 |
| Poloxamer 407, NF | | | | | | | | 20.000 |
| Silica Abrasive | 20.000 | 20.000 | 20.000 | 10.000 | 10.000 | 20.000 | 20.000 | |
| Sodium Fluoride | 0.243 | 0.243 | 0.243 | 0.243 | 0.243 | 0.243 | 0.243 | 0.243 |
| Na Alkyl Sulfate Soln. (28%) | 4.000 | 4.000 | 4.000 | 4.000 | 4.000 | 4.000 | 4.000 | |
| Polysiloxane Functionalized with Malic Acid | 3.000 | | 5.000 | 3.000 | 3.000 | 1.000 | 5.000 | 4.000 |
| Polysiloxane Functionalized with Phthalic Acid | | 3.000 | | | | | | |
| Urea Peroxide | | | | 3.500 | 10.000 | | | |
| Triclosan | | | | | | 0.300 | | |
| Vitamin E | | | | | | | 5.000 | |
| Cetyl Pyridinium Chloride (CPC) | | | | | | | | 1.000 |
| Titanium Dioxide | 0.020 | 0.020 | 0.020 | 0.020 | 0.020 | 0.020 | 0.020 | 0.020 |
| Na Benzoate/Benzoic Acid | | | | | | | 0.600 | |
| Water, Purified USP | QS | QS | QS | QS | QS | QS | QS | QS |

Example 3

Mouthrinse

| Components | Weight % |
|---|---|
| Water | 29.000 |
| Propylene Glycol | 53.459 |
| Sodium Benzoate | 0.320 |
| Benzoic Acid | 0.021 |
| Sodium Saccharin | 0.700 |
| Polysiloxane Functionalized with Malic Acid | 5.000 |
| Poloxamer 407 | 10.000 |
| Flavor | 1.500 |

Example 3 is prepared as follows: Mix water, poloxamer and propylene glycol. Next add the flavor, benzoic acid, and the siloxane polymer. Finally add the sodium benzoate and sodium saccharin and mix until homogeneous.

Example 4

Chewing Gum

Chewing gum compositions including a coated chewing gum (4C) according to the present invention are shown below and made as follows.

| Components | 4A | 4VIIB |
|---|---|---|
| Xylitol | 16.700 | 16.700 |
| Gum base (e.g., Prestige-PL, Cafosa) | 28.000 | 28.000 |
| Polysiloxane Functionalized with Malic Acid | 5.000 | 5.000 |
| Urea Hydrogen Peroxide | | 10.000 |
| Hydrogenated starch hydrolysate (85% solids) | 8.000 | 8.000 |
| Glycerin | 7.000 | 7.000 |
| Mannitol | 5.000 | 5.000 |
| Flavor | 1.600 | 1.600 |
| Aspartame | 0.200 | 0.200 |
| Spray dried menthol | 0.150 | 0.150 |
| Sorbitol | QS | QS |

Making Instructions

Examples 4A and 4B

Heat gum base to ~45° C. to soften. Maintain mixer vessel cavity at ~45° C. during entire mixing process. Add gum base to mixing cavity of double sigma blade mixer and mix for 5 minutes. Add mannitol and spray-dried menthol. Mix for 2 minutes. Add glycerin and mix for 2 minutes. Add 50% of xylitol and mix for 2 minutes. Add hydrogenated starch hydrolysate and mix for 5 minutes. Add 50% sorbitol and mix for 3 minutes. Add second 50% of xylitol, siloxane polymer, and aspartame and mix for 3 minutes. Add flavor and mix for 3 minutes. In the case of 4B, add the bleach toward the end at close to room temperature to minimize active oxygen loss.

| 4C Components | Core 1 g/piece | Coating 0.35 g/piece | Total 1.35 g/piece |
|---|---|---|---|
| Sorbitol | 49.35 | — | 36.55 |
| Gum base[1] | 25.0 | — | 18.52 |
| Polysiloxane Functionalized with Malic Acid | 5.0 | — | 7.41 |
| Urea Hydrogen Peroxide | 5.0 | — | 7.41 |
| Sodium fluoride | — | 0.08 | 0.02 |
| Xylitol | — | — | — |
| Hydrogenated Starch Hydrolysate | 5.0 | — | 3.70 |
| Mannitol | 2.0 | — | 1.48 |
| Glycerin | 5.0 | — | 3.70 |
| Titanium dioxide | — | 2.0 | 0.52 |
| Flavor | 2.0 | 2.0 | 2.00 |
| Additional spray-dried flavor | 1.5 | — | 1.11 |
| Sucralose | 0.05 | 0.03 | 0.05 |
| Potassium Acesulfame | 0.10 | 0.10 | 0.10 |
| Sorbitol[2] | — | 95.25 | 24.70 |
| Polysorbate 60 | — | 0.30 | 0.08 |
| Insoluble edible glitter[3] (Brilliant Blue) | — | 0.04 | 0.01 |
| Wax[4] | — | 0.20 | 0.05 |

[1]Comprises several ingredients, including pre-supplied gum bases from suppliers such as L. A. Dreyfus Company, 3775 Park Avenue, Edison, New Jersey, US; Cafosa Gum, Calabria 267, 08029, Barcelona, Spain, etc.
[2]Level of sorbitol refers to absolute level after drying; sorbitol is added as a 70% aq. soln.
[3]Supplied by Watson Foods Company Incorporated, 301 Heffernan Drive, West Haven, Connecticut, USA.

-continued

| 4C Components | Core 1 g/piece | Coating 0.35 g/piece | Total 1.35 g/piece |
|---|---|---|---|

[4] Level of wax refers to absolute level after drying wax is added as a 28% ethanolic solution; wax used comprises several ingredients such as that supplied by Kaul GmBH, Elmshorn, Germany Making Instructions Example 4C Core Formulation: Soften gum base with gentle heating and add mannitol, spray-dried flavor, glycerin, 50% of xylitol, hydrogenated starch hydrolysate, 50% of sorbitol and mix thoroughly. Add second 50% of xylitol, siloxane polymer and urea hydrogen peroxide (when needed) and aspartame, remainder of flavor and mix further. Form bulk chewing gum mass into discrete pieces of desired shape and size using rolling and scoring equipment.

Coating Solution: Add titanium dioxide and Polysorbate 60 to 70% aqueous sorbitol solution and mix. Add flavor followed by Sucralose and Potassium Acesulfame and-mix further.

Coating of Core Formulation: Place gum pieces into a coating pan and apply coating solution, partially dry. Repeat coating step until desired coating thickness or weight is achieved. Apply clear 70% aqueous sorbitol solution and, whilst wet, dry spray speckles onto product surface, dry. Apply second coat of clear 70% sorbitol solution followed by wax coating and allow product to fully dry.

Example 5

Antimicrobial Skin Cleansing Lotions

The following are non-limiting examples of the skin cleansing compositions of the present invention. A suitable method for preparing the skin cleansing lotions described in Examples 5A–5C (below) follows. In a suitable container, the pyroglutamic acid, sodium chloride and water are added and mixed with stirring until mixture is homogeneous. Sodium benzoate, tetrasodium EDTA and surfactant(s) are then added to the mixture with stirring and mixed until the ingredients are completely dissolved. Once dissolved, the antimicrobial agent and DC Antiform H-10 are added to the mixture with stirring. In a separate container, the perfume and ethanol are mixed to form a premix. The premix is then added to the mixture to form the aqueous lotion. The aqueous lotion is pH adjusted to about 3.0 using NaOH or HCl. The aqueous lotion is applied to the skin in an appropriate amount to disinfect and cleanse the skin.

| Component | 5A | 5B | 5C |
|---|---|---|---|
| Triclosan | 0.1 | 0.1 | 0.25 |
| Cocamine Oxide (C10/C16 alkyl dimethyl amine oxide)[1] | 0.5 | | |
| Ammonium Lauryl Sulfate | | 0.6 | 0.6 |
| Pyroglutamic Acid (2-pyrrolidone-5 carboxylic acid) | 4.0 | 4.0 | 4.0 |
| Polysiloxane Functionalized with Malic Acid | 0.5 | 1.0 | 2.0 |
| Ethanol-denatured 200 proof (SD alcohol 40) | 10.0 | 10.0 | 10.0 |
| DC Antiform H-10 (dimethicone) | 0.03 | 0.03 | 0.03 |
| Sodium Benzoate | 0.2 | 0.2 | 0.2 |
| Tetrasodium | 0.1 | 0.1 | 0.1 |

-continued

| Component | 5A | 5B | 5C |
|---|---|---|---|
| Sodium Chloride | 0.4 | 0.4 | 0.4 |
| Tospearl 2000[2] | — | — | 2.0 |
| Perfume | 0.01 | 0.01 | 0.01 |
| Water and minors | QS | QS. | QS. |
| NaOH or HCl for pH adjustment to pH = 3.0 | | | |

[1] AO-1214 LP supplied by The Procter & Gamble Co.
[2] Tospearl tradename of crosslinked hydrocarbyl-substituted polysiloxane available from Toshiba Silicone Example 6

Antimicrobial Cleansing Wipes

The aqueous lotions of Example 5 can alternatively be applied onto a substrate at a lotion to substrate weight ratio of about 2:1 using conventional substrate coating techniques to prepare antimicrobial and cleansing wipes for use on skin. An example of a water-insoluble substrate useful in the present invention is a patterned hydroentangled non-woven substrate having a basis weight of 56 gms, comprising 70% polyester and 30% rayon approximately 6.5 inches wide by 7.5 inches long with a caliper of about 0.80 mm. Optionally, the substrate can be pre-coated with dimethicone (Dow Corning 200 Fluid 5cst) using conventional substrate coating techniques.

Example 7

Lotioned Topsheet

A lotion composition is made by mixing the following melted (i.e., liquid) components together: White Protopet® 1S (white petrolatum made by Witco Corp.); Dow Corning 556 Cosmetic Grade Fluid (a polyphenylmethylsiloxane made by the Dow Corning Corporation), Parrafin S.P. 434 (a paraffin wax made by Strahl and Pitsch Inc.); Cetearyl Alcohol (a mixed linear $C_{16}$–$C_{18}$ primary alcohol made by the Procter & Gamble Company under the name TA-1618); PEG 2000 (a polyethylene glycol having a MW of 2000 made by Sigma-Aldrich Corp). The weight percentages of these components are shown below:

| Components | Weight % |
|---|---|
| WhiteProtopet ® 1S | 52 |
| Malic Acid Functionalized Polysiloxane | 20 |
| Paraffin Wax | 15 |
| Cetearyl Alcohol | 10 |
| PEG 2000 | 3 |

The lotion composition is placed into a heated tank operating at a temperature of 150° F. The composition is subsequently sprayed (using a Dynatec E84B1758 spray head, operating at a temperature of 170° F. and an atomization pressure of 2.40 psig) onto the topsheet of a diaper in a 3.75 inch wide (diaper lateral direction) and 7 inch long (diaper longitudinal direction) area, the patch beginning 1 inch forward of the lateral centerline and extending toward the rear of the product. Add-on level=0.006 g/in$^2$ (9.3 g/m$^2$).

Example 8

Shampoo Compositions

The following are non-limiting examples of anti-dandruff and conditioning shampoo compositions of the present invention. As used herein, "minors" refers to those optional components such as preservatives, viscosity modifiers, pH modifiers, fragrances, foam boosters, and the like. As is apparent to one of ordinary skill in the art, the selection of these minors will vary depending on the physical and chemical characteristics of the particular ingredients selected to make the present compositions as described herein.

A suitable method for preparing the anti-dandruff and conditioning shampoo compositions described in Examples 8A–8E (below) follows: About one-third to all of the ammonium laureth sulfate (added as 25 wt % solution) is added to a jacketed mix tank and heated to about 60° C. to about 80° C. with slow agitation to form a surfactant solution. Cocamide MEA and fatty alcohols, (where applicable), are added to the tank and allowed to disperse. Salts (e.g. sodium chloride) and pH modifiers (e.g. citric acid, sodium citrate) are added to the tank and allowed to disperse. Ethylene glycol distearate ("EGDS") is added to the mixing vessel and allowed to melt. After the EGDS is melted and dispersed, preservative is added to the surfactant solution. The resulting mixture is cooled to about 25° C. to about 40° C. and collected in a finishing tank. As a result of this cooling step, the EGDS crystallizes to form a crystalline network in the product. The remainder of the ammonium laureth sulfate and other components, including the siloxane polymer and anti-dandruff agent, are added to the finishing tank with agitation to ensure a homogeneous mixture. Cationic polymer is dispersed in water as an about 0.1% to about 10% aqueous solution and then added to the final mix. Once all components have been added, additional viscosity and pH modifiers may be added, as needed, to the mixture to adjust product viscosity and pH to the extent desired.

| Components | 8A | 8B | 8C | 8D | 8E |
|---|---|---|---|---|---|
| Ammonium Laureth Sulfate | 11.0 | 9.0 | 10.0 | 10.0 | 11.5 |
| Ammonium Lauryl Sulfate | 6.0 | 7.0 | 6.0 | 7.0 | 6.5 |
| Polyquaternium-10[1] | 0.35 | 0.35 | 0.5 | 0.1 | 0.45 |
| Guar Hydroxypropyltrimonium Chloride[2] | 0.25 | 0.25 | — | 0.4 | — |
| PEG7M[3] | 0.1.0 | 0.05 | 0.1 | 0.05 | 0.15 |
| Zinc Pyrithione[4] | 1.0 | 1.0 | 1.0 | 1.0 | 1.0 |
| 1-decene homopolymer[5] | 0.25 | 0.4 | 0.3 | 0.25 | 0.3 |
| Trimethylpropane Capryl Caprylate[6] | 0.1 | 0.2 | 0.1 | 0.1 | 0.15 |
| Malic Acid Functionalized Polysiloxane | 2.55 | 3.25 | 1.35 | 3.25 | 2.55 |
| Ethylene Glycol Distearate | 1.25 | 1.0 | 1.5 | 1.0 | 1.5 |
| Cocamide MEA | 1.0 | 0.6 | 0.8 | 0.6 | 0.8 |
| Cetyl Alcohol | 0.6 | 0.6 | 0.9 | 0.9 | 1.0 |
| Water and minors | QS | QS | QS | QS | QS |

[1]UCARE Polymer LR400, available from Amerchol.
[2]Guar having a molecular weight of about 200,000, and having a charge density of about 0.71 meq/g, available from Aqualon.
[3]Polyox WSR N-750, available from Union Carbide.
[4]ZPT with average particle size of about 2.5 μm, available from Arch/Olin.
[5]Puresyn 6, available from Mobil.
[6]Mobil P43, available from Mobil.

Example 9

Laundry Compositions

The following are non-limiting examples of laundry compositions according to the present invention, which can be suitably prepared by any process chosen by the formulator.

| Components | 9A | 9B | 9C | 9D |
|---|---|---|---|---|
| Sodium $C_{11}$–$C_{13}$ alkylbenzene-sulfonate | 13.3 | 13.7 | 10.4 | 11.1 |
| Sodium $C_{14}$–$C_{15}$ alcohol sulfate | 3.9 | 4.0 | 4.5 | 11.2 |
| Sodium $C_{14}$–$C_{15}$ alcohol ethoxylate (0.5) sulfate | 2.0 | 2.0 | — | — |
| Sodium $C_{14}$–$C_{15}$ alcohol ethoxylate (6.5) | 0.5 | 0.5 | 0.5 | 1.0 |
| Tallow fatty acid | — | — | — | 1.1 |
| Sodium tripolyphosphate | — | 41.0 | — | — |
| Zeolite A, hydrate (0.1–10 micron size) | 26.3 | — | 21.3 | 28.0 |
| Sodium carbonate | 23.9 | 12.4 | 25.2 | 16.1 |
| Sodium Polyacrylate (45%) | 3.4 | — | 2.7 | 3.4 |
| Sodium silicate (1:6 ratio $NaO/SiO_2$)(46%) | 2.4 | 6.4 | 2.1 | 2.6 |
| Sodium sulfate | 10.5 | 10.9 | 8.2 | 15.0 |
| Sodium perborate | 1.0 | 1.0 | 5.0 | — |
| Poly(ethyleneglycol), MW ~4000 (50%) | 1.7 | 0.4 | 1.0 | 1.1 |
| Citric acid | — | — | 3.0 | — |
| Bleach catalyst[1] | 0.035 | 0.030 | 0.034 | 0.028 |
| Bleach activator[2] | — | — | 5.9 | — |
| Functionalized Siloxane Polymer[3] | 2.00 | 3.00 | 2.50 | 2.50 |
| Suds suppressor | 0.60 | 0.60 | 0.60 | 0.60 |
| Water and minors[4] | balance | balance | balance | balance |

[1]1,5-bis(hydroxymethylene)-3,7-dimethyl-2,4-bis(2-pyridyl)-3,7-diazabicyclo[3.3.1]-nonan-9-ol manganese(II) dichloride 1/2H₂O.
[2]Nonyl ester of sodium p-hydroxybenzene-sulfonate.
[3]Polysiloxane Functionalized with Malic Acid or Polysiloxane Functionalized with Phthalic Anhydride
[4]Balance to 100% can, for example, include minors like optical brightener, perfume, soil dispersant, chelating agents, dye transfer inhibiting agents, additional water, and fillers, including $CaCO_3$, talc, silicates, etc.

Example 10

Hard Surface Cleaning Compositions

The following non-limiting examples illustrate hard surface cleaners of the present invention, which can be suitably prepared by any process chosen by the formulator.

| Components | 10A | 10B | 10C | 10D |
|---|---|---|---|---|
| $C_{11}EO_5$ | 7.0 | 14.0 | 14.0 | — |
| $C_{11}EO_7$ | — | — | — | 7.0 |
| $C_{10}EO_7$ | 7.0 | — | — | 7.0 |
| Trisodium citrate | 1.0 | 1.0 | — | 1.0 |
| Potassium carbonate | 0.2 | 0.2 | 0.2 | 0.2 |
| Triethanol amine | — | — | 1.0 | — |
| Malic Acid Functionalized Polysiloxane | 0.10 | 0.50 | 0.25 | 1.0 |
| N-2-propylheptyl sulfosuccinamate | 3.0 | 3.0 | 3.0 | 3.0 |
| Perfume | 1.0 | 1.0 | 1.0 | 1.0 |
| Alkalinity adjusted to pH | 10.5 | 10.5 | 7.4 | 10.5 |
| Water, salts, fillers | balance | balance | balance | balance |

Example 11

Denture Adhesive Compositions

Denture adhesive compositions in cream form can be made by blending together the following ingredients.

| Components | 11A | 11B | 11C | 11D |
|---|---|---|---|---|
| White Mineral Oil | 23.93 | 23.93 | 23.93 | 0 |
| Petrolatum, White | 21.77 | 20.87 | 11.87 | 0 |
| Carboxymethylcellulose Sodium | 20.00 | 20.00 | 20.00 | 20.00 |
| Silicon Dioxide, Colloidal | 1.14 | 1.14 | 1.14 | 1.14 |
| Colorant (Opatint Red Dye) | 0.06 | 0.06 | 0.06 | 0.06 |
| Functionalized Siloxane Polymer[1] | 0.10 | 1.00 | 10.00 | 45.8 |
| Alkyl Vinyl Ether/Maleic Acid (AVE/MA) Copolymer Salt | 33.00 | 33.00 | 33.00 | 33.00 |

[1]Polysiloxane Functionalized with Malic Acid or Polysiloxane Functionalized with Phthalic Anhydride Mix the fluid components (red dye, Functionalized Polysiloxane, petrolatum, mineral oil) at 50 to 60° C. until visually uniform. Then shake-blend the powder components (colloidal silicon dioxide, CMC, any AVE/MA copolymer mixed salt) together in a container. Thereafter, mix the powders into the liquid forming a uniform pink cream. The cream compositions may be modified by increasing or decreasing the levels of each of the AVE/MA salt of, petrolatum, and/or the CMC by up to 10 grams. The above cream compositions can also be modified by using mixtures of various AVE/MA mixed polymer salts, such as Ca/Zn or Mg/Ca/Zn salts, and/or acid. In use the subject places from 0.1 to 2 grams of the cream composition on the denture. Then the subject inserts the denture into his/her mouth and presses it into place.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for cleaning, conditioning and disinfecting fibers, fabrics and hard surfaces, comprising
   (a) at least about 0.001% by weight of an anionic functionalized siloxane polymer of formula

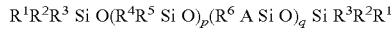

wherein
   $R^1$ to $R^6$, which may be identical or different, each represents a linear or branched C1–C8 alkyl or a phenyl radical;
   A represents a carboxy group containing radical of formula

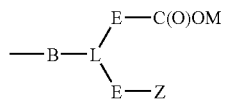

wherein B represents an alkylene residue having from 2 to 30 carbon atoms, optionally interrupted by up to 8 non-neighboring oxygen atoms or groups of the formula —$NR^7$—, —CO— or —C(O)—O—C(O)—, wherein $R^7$ is hydrogen or C1–C4 alkyl,
   L represents CR' or phenyl, wherein R' represents a hydrogen atom, an alkyl radical having from 1 to 30 carbon atoms or a carboxy group,
   E is nil or is an alkylene residue having from 1 to 5 carbon atoms, optionally substituted by one or more alkyl radicals having from 1 to 8 carbon atoms,
   Z represents an anionic functional group selected from hydroxy, amino, carboxy, or alkoxy, wherein when L is CR', Z is other than carboxy and when L is phenyl, the groups -E-C(O)OM and -E-Z are ortho to each other and E is nil, and
   M is H an alkyl group having from 1 to 4 carbon atoms optionally substituted with a hydroxy or alkoxy groups or a cation selected from the group consisting of alkali metal, alkaline earth metal, and substituted or non substituted ammonium, piperidinium or alkanolamine;
   p is an average value ranging from 0 to 1000; and
   q is an average value ranging from 1 to 100, and
   b) at least one surfactant and at least one additive or active agent selected from acidic cleaning agents, metal chelating agents, calcium-sequestering agents, hydrotropic agents, bleaching agents, abrasives, corrosion inhibitors, anti-redeposition agents, anti-color transfer agents, and soil-release agents,
   wherein the amounts of anionic functionalized siloxane polymer, surfactant and additive or active agent are effective to clean, rinse, repair, care for or treat surfaces selected from fibers, textiles, leather, paper, plastic, wood, metal, glass, stone and concrete.

2. A composition for treating surfaces containing cationic sites, comprising at least about 0.001% by weight of an anionic functionalized siloxane polymer of formula

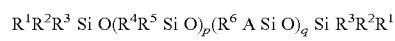

wherein
   $R^1$ to $R^6$, which may be identical or different, each represents a linear or branched C1–C8 alkyl or a phenyl radical;
   A represents a carboxy group containing radical selected from one or a combination of:

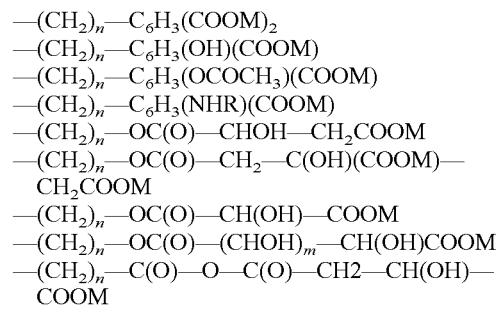

wherein n is from 2 to 30, in is from 2 to 4 and R is H or C1–C8 alkyl and M is H, an alkyl group having from 1 to 4 carbon atoms optionally snbstituted with a hydroxy or alkoxy groups or a cation selected from the group consisting of alkali metal, alkaline earth metal, and substituted or non substituted ammonium, piperidinium or alkanolamine;
   p is an average value ranging from 0 to 1000; and
   q is an average value ranging from 1 to 100,
   wherein the anionic functionalized siloxane polymer is present in an amount effective to hydrophobically modify said surfaces.

3. A composition for oral care use comprising
   (a) an orally acceptable carrier;

(b) a safe and effective amount of at least one oral care agent suitable for administration to a subject's oral cavity, selected from the group consisting of a bleaching agent, whitening agent, anti-tartar agent, anticanes agent, H2 antagonist, analgesic, anti-viral agent, denture adhesive, flavoring agent, fluoride ion source, abrasive, desensitizing agent, chelating agent and mixtures thereof; and (c) at least about 0.1% by weight of a dicarboxy functionalized siloxane polymer suitable for administration to a subject's oral cavity, of formula

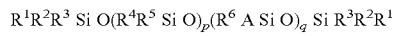

wherein $R^1$ to $R^6$, which may be identical or different, each represents a linear or branched C1–C8 alkyl or a phenyl radical;

A represents a carboxy group containing radical of formula

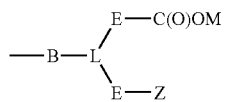

wherein B represents an alkylene residue having from 2 to 30 carbon atoms, optionally interrupted by up to 8 non-neighboring oxygen atoms or groups of the formula —$NR^7$—, —CO— or —C(O)—O—C(O)—, wherein $R^7$ is hydrogen or C1–C4 alkyl, L represents CR' or phenyl, wherein R' represents a hydrogen atom, an alkyl radical having from 1 to 30 carbon atoms or a carboxy group, E is nil or is an alkylene residue having from 1 to 5 carbon atoms, optionally substituted by one or more alkyl radicals having from 1 to 8 carbon atoms, Z represents an anionic functional group selected from hydroxy, amino, carboxy, or alkoxy, wherein when L is CR', Z is other than carboxy and when L is phenyl, the groups -E-C(O)OM and -E-Z are ortho to each other and E is nil, and M is H, an alkyl group having from 1 to 4 carbon atoms optionally substituted with a hydroxy or alkoxy groups or a cation selected from the group consisting of alkali metal, alkaline earth metal, and substituted or non substituted ammonium, piperidinium or alkanolamine;

p is an average value ranging from 0 to 1000; and q is an avenge value ranging from 1 to 100, wherein the composition is effective to provide one or more benefits to oral cavity surfaces.

4. A composition for oral care use comprising (a) a bleaching agent of from about 0.1% to about 20.0% by weight of the composition, and (b) at least about 0.1% by weight of a dicarboxy functionalized siloxane polymer suitable for administration to a subject's oral cavity of formula

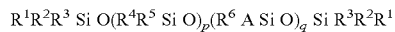

wherein

R to $R^6$, which may be identical or different, each represents a liner or branched C1–C8 alkyl or a phenyl radical;

A represents a carboxy group containing radical of formula

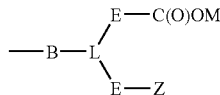

wherein B represents an alkylene residue having from 2 to 30 carbon atoms, optionally interrupted by up to 8 non-neighboring oxygen atoms or groups of the formula —$NR^7$—, —CO— or —C(O)—O—C(O)—, wherein $R^7$ is hydrogen or C1–C4 alkyl.

L represents CR' or phenyl, wherein R' represents a hydrogen atom, an alkyl radical having from 1 to 30 carbon atoms or a carboxy group, E is nil or is an alkylene residue having from 1 to 5 carbon atoms, optionally substituted by one or more alkyl radicals having from 1 to 8 carbon atoms, Z represents an anionic functional group selected from hydroxy, amino, carboxy, or alkoxy, wherein when L is CR', Z is other than carboxy and when L is phenyl, the groups -E-C(O)OM and -E-Z are ortho to each other and E is nil, and M is H, an alkyl group having from 1 to 4 carbon atoms optionally substituted with a hydroxy or alkoxy groups or a cation selected from the group consisting of alkali metal, alkaline earth metal, and substituted or non substituted ammonium, piperidinium or alkanolamine;

p is an average value ranging from 0 to 1000; and q is an avenge value ranging from 1 to 100.

5. A composition for oral care use according to claim 4 wherein the bleaching agent is selected from the group consisting of peroxides, perborates, percarbonates, peroxyacids, persulfates, metal chlorites, and mixtures thereof.

6. A composition for oral care use according to claim 5 wherein the bleaching agent is selected from the group consisting of hydrogen peroxide, urea peroxide, calcium peroxide, sodium percarbonate, sodium chlorite, potassium chlorite and mixtures thereof.

7. A method of cleaning and whitening a subject's teeth or dental prosthesis; preventing or reducing plaque, caries, calculus and stains on teeth or dental prosthesis; and providing shine, smoothness and positive feel benefits to teeth, comprising administering to the subject's oral cavity a composition according to claim 2.

8. A method of cleaning and whitening a subject's teeth or dental prosthesis; preventing or reducing plaque, caries, calculus and stains on teeth or dental prosthesis; and providing shine, smoothness and positive feel benefits to teeth, comprising administering to the subject's oral cavity a composition according to claim 3.

9. A method of enhancing efficacy of compositions for treating surfaces containing cationic sites comprising adding to said compositions a carrier for active agents comprising an anionic functionalized siloxane polymer according to claim 2 in an amount effective to hydrophobically modify said surfaces and to enhance deposition and retention of said active agents on said treated surfaces.

* * * * *

UNITED STATES PATENT AND TRADEMARK OFFICE
CERTIFICATE OF CORRECTION

PATENT NO. : 7,166,235 B2
APPLICATION NO. : 10/430520
DATED : January 23, 2007
INVENTOR(S) : Satyanarayana Majeti et al.

It is certified that error appears in the above-identified patent and that said Letters Patent is hereby corrected as shown below:

Column 30
Line 54, delete "in" and insert --m--.

Column 31
Line 61, delete "Rto" and insert --$R^1$ to--.

Signed and Sealed this

Twenty-fourth Day of July, 2007

JON W. DUDAS
*Director of the United States Patent and Trademark Office*